United States Patent [19]

Michnick et al.

[11] Patent Number: 4,512,744

[45] Date of Patent: Apr. 23, 1985

[54] METHOD ENABLING RAPID IDENTIFICATION OF HUMANS AND ANIMALS

[75] Inventors: Bruce T. Michnick, Plainview; Stanley Kitzis, Woodbury, both of N.Y.

[73] Assignee: Dentistry Researchers & Designers, Inc.

[21] Appl. No.: 546,375

[22] Filed: Oct. 28, 1983

[51] Int. Cl.³ .......................... A61C 3/00; A61B 1/24
[52] U.S. Cl. ................................................... 433/229
[58] Field of Search ............................... 433/215, 229

[56] References Cited

U.S. PATENT DOCUMENTS

Re. 30,594  4/1981  Samis ................................. 433/229
4,439,154  3/1984  Mayclin ............................. 433/229

Primary Examiner—Robert Peshock
Attorney, Agent, or Firm—Charles I. Brodsky

[57] ABSTRACT

Message identifying information in available microdot format is applied to a tooth preparation of a prescribed depth, where it can be easily coated over with a clear composite, yet still readable by appropriate scanning devices.

6 Claims, No Drawings

METHOD ENABLING RAPID IDENTIFICATION OF HUMANS AND ANIMALS

FIELD OF THE INVENTION

This invention relates to the science of identification, in general, and to a method for rapidly identifying humans and animals, in particular.

BACKGROUND OF THE INVENTION

As is well known and understood, several methods are employed in identifying the remains of those killed in accidents, disasters, and/or natural and man-made cataclysmic holocausts. If photographs are not helpful, resort is often made to the use of fingerprints as a means of identification—but the problem with that is that those whose fingerprints are on file represent only an infinitesimal number of persons, and the fingerprinting of school-age children is just beginning, although continuing to be met with resistance. Dental records are employed, but only after some idea exists as to the identity of the person sought to be substantiated, and, really, of limited usefulness. While the use of "dog-tags" in the military continues to be a common practice, instances often arise where the "dog-tags" are destroyed, missing, or otherwise not available for purposes of identification.

And, no matter what the above restrictions offer as regards the identification of humans, the identification of animals is a far greater problem. Besides the issuance of license tags—except for photographs of the animals in question, or the availability of other visual indicia—the only technique usually available involves a process of "branding", limited to race-horses and cattle, in general.

DETAILED DESCRIPTION OF THE INVENTION

In accordance with the method of the invention, microdot technology is combined with readily available and understood dental techniques in applying the message identifying information characteristics to a tooth preparation in simple, inexpensive manner. In accordance with present day techniques, the microdot can have inscribed upon it any and all information pertaining to the human or animal—such as social security numbers, name, address and telephone information, fingerprint designations, health information, serial numbers for animals, and any other indicia of identification desired. Such information can be inscribed on a microdot in any available technology—such as with alphanumerics, strip, disc or bar-line codes—, and can be inscribed on either a plastic, paper, or metal disc of an approximate 4 millimeter size. In a preferred embodiment of the present invention, such encoded disc is embedded in prescribed manner on the tooth of the human, or animal, with a lower right molar in humans being particularly attractive. Such attractiveness results from the ease in which visual scanners, and/or laser-beam techniques can be utilized in "reading" the information on the tooth face.

In carrying out the method of the invention, a self-limiting dental drill is utilized, corresponding to the size of the microdot or microdisc. With such drill, the tooth face can be prepared to a predetermined depth of an amount requiring no anaesthesia. Although a dental drill is especially easy for preparing an initial cavity for the insertion of the information disc, other preparation techniques may be employed—e.g. the use of laser beams, ultrasonic drilling, etc.

Once the drilling or other means has been utilized to provide the depth required, a standard "acid-etching technique" can be utilized, in which an acid (typically 35% to 50% stabilized phosphoric acid) is applied to the area in question for approximately 60 seconds. After washing with water and drying, the disc can be placed in the prepared area under contamination free conditions. Once the disc is allowed to dry, a layer of clear, composite material can be applied to cover the informational disc and to fill the cavity established. Such a composite resin thus embeds the disc in the tooth, to become a permanent identification record. One such composite resin which can be employed is marketed under the brandname "COMPLUS", by the Parkel Company of Farmingdale, N.Y. Such composite, however, can be any appropriate white light cured material, or a catalyst, e.g. BIS GMA, induced composite.

When so prepared, the tooth—be it of a human or of an animal—is marked for life. If an occasion thereafter arises by which some means of identification is required, an available scanning technique, even using handheld apparatus, can be employed. Dependent upon the information imparted to the microdot or other informational disc, an investigator can identify the individual, and can be provided with other emergency information, as medical status, allergy information, persons to contact in cases of emergency, etc., as well as all the identification information alluded to above. As will be seen, depending upon what is to be imparted to the disc implanted in either the human or animal tooth, the benefits to be derived are numerous, with but a simple technique which, at the same time, is cost effective. The ability to gather this kind of information in a quick, efficient manner, will give advantages which will be readily available to those to whom such information is useful.

While there has been described what is considered to be a preferred embodiment of the present invention, it will be readily appreciated by those skilled in the art that modifications can be made without departing from the scope of the teachings herein. For example, although the invention has been described in the context of the utilization of a microdot or other informational disc, it will equally be seen that the information indicia can be incorporated as part of a computer chip, or magnetic tape, as well as of other materials as well. Similarly, although a preferred form of the invention envisions the placement of such information on the "cheek" side of a tooth, it will be appreciated that the incorporation could be on the "tongue" side of the tooth, and still operate in accordance with the invention. And, it would be equally clear that the information indicia could be affixed not only to a "real" tooth—but, in the case of humans, could be imparted in connection with usage in a denture or in a crown, depending upon the particular findings in the patient's mouth. For at least such reasons, therefore, resort should be had to the claims appended hereto for a correct understanding of the breadth of its coverage.

We claim:

1. A method enabling identification of human and animal subjects, comprising the steps of:
 a. first, permanently affixing an indicia of identification information at a location within a face surface of a tooth of the subject which can be viewed by another looking into the subject's mouth; and b. second, electronically scanning said identifying indicia from outside the subject's mouth, for non-destructively out-putting the information thereby stored thereon.

2. The method of claim 1 wherein said first step affixes a microdot to said tooth face surface containing the information indicia pertaining to the subject to be identified.

3. The method of claim 1 wherein said first step affixes the information indicia to said tooth face surface to a predetermined depth.

4. The method of claim 3 wherein said first step includes the sub-steps of:

a. first, preparing a cavity within said tooth face surface to receive said information indicia at said predetermined depth;
b. second, placing said information indicia within said cavity;
c. thid, layering a clear composite material over said indicia to protect said indicia and to fill the cavity so formed.

5. The method of claim 4 wherein said first sub-step includes the step of using a self-limiting dental drill to prepare said tooth face cavity of a size corresponding to that of said information indicia.

6. The method of claim 4 wherein said second sub-step includes the step of cleansing said information incidia of contamination prior to the layering thereover of said composite material in said third sub-step.

* * * * *